United States Patent

Yoshikawa et al.

Patent Number: 4,885,367
Date of Patent: Dec. 5, 1989

[54] SULFONANILIDE COMPOUNDS

[75] Inventors: Kensei Yoshikawa; Yutaka Ohuchi, both of Urawa; Kazuto Sekiuchi, Ageo; Shiuji Saito; Katsuo Hatayama, both of Omiya; Kaoru Sota, Tokorozawa, all of Japan

[73] Assignee: Taisho Pharmaceutical Co., Ltd., Japan

[21] Appl. No.: 271,641

[22] Filed: Nov. 16, 1988

[30] Foreign Application Priority Data

Nov. 19, 1987 [JP] Japan ................... 62-292856

[51] Int. Cl.$^4$ ................. C07D 211/46; C07D 335/04; C07D 313/00; C07C 143/78
[52] U.S. Cl. ..................................... 546/216; 549/28; 549/419; 564/97; 564/99
[58] Field of Search .................. 564/99, 219, 97; 568/30; 514/605; 546/216, 217, 233; 549/28, 419

[56] References Cited

U.S. PATENT DOCUMENTS 3,856,859  12/1974  Moore et al. ................. 564/99
4,529,730  7/1985  Schneider et al. ............. 546/216

Primary Examiner—Richard L. Raymond
Assistant Examiner—Kristina L. Konstas
Attorney, Agent, or Firm—Lorusso & Loud

[57] ABSTRACT

Sulfonanilide compounds represented by the formula

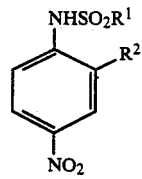

wherein $R^1$ is a lower alkyl group or a trifluoromethyl group, $R^2$ is a cycloalkylidenemethyl group, a group of the formula —A—$R^3$ (wherein A is an oxygen atom, a sulfur atom, a sulfynyl group or a sulfinyl group and $R^3$ is a cycloalkyl group having 5–8 carbon atoms; a cycloalkyl group having 5–8 carbon atoms substituted by one or two of a lower alkyl group, an oxo group, a hydroxyl group or a methanesulfonyloxy group, a tetrahydropyranyl group; a tetrahydrothiopyranyl group; or a 1-methyl-piperidyl group) or a group of the formula —B—$R^4$ (wherein B is a carbonyl group, a hydroxymethylene group or a methylene group, $R^4$ is a cycloalkyl group having 5–8 carbon atoms) and the pharmaceutically acceptable salts thereof have anti-inflammatory activity.

1 Claim, 1 Drawing Sheet

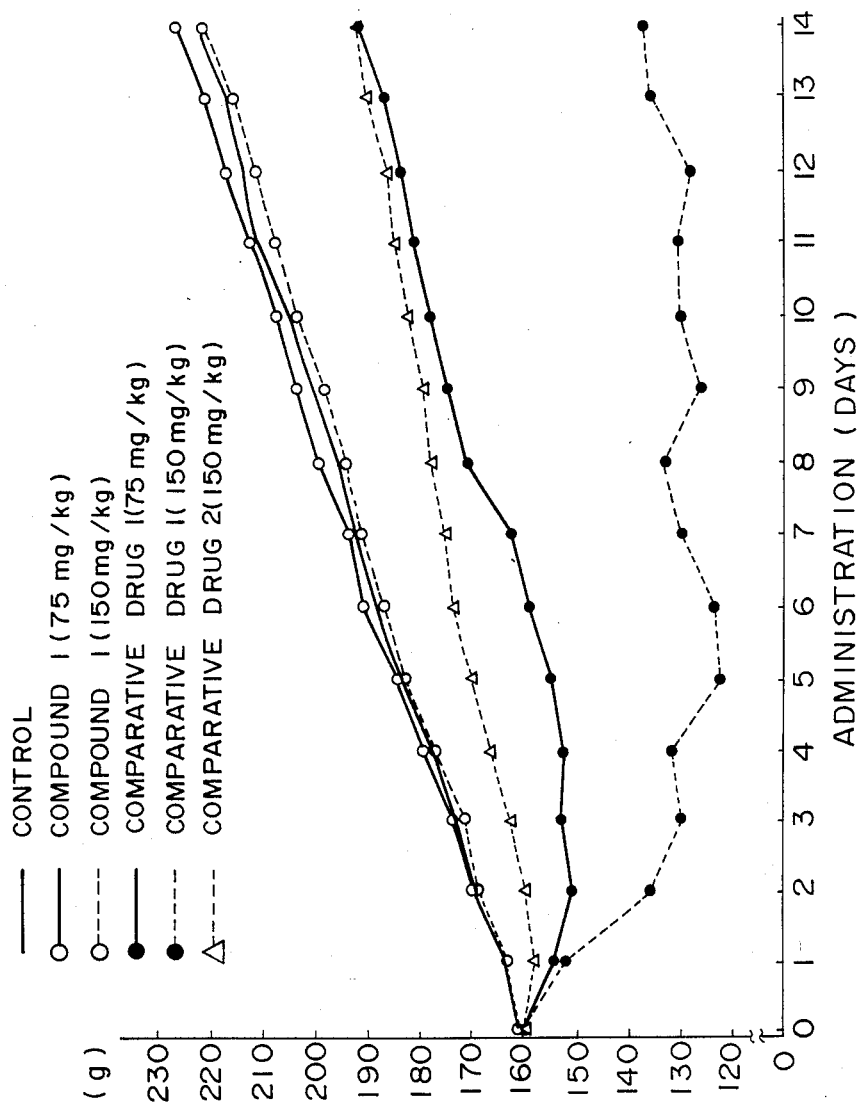

SULFONANILIDE COMPOUNDS

BACKGROUND OF THE INVENTION

1. Field of the Invention

The present invention relates to sulfonanilide compounds and more particularly sulfonanilide compounds and the pharmaceutically acceptable salts thereof having anti-inflammatory effect.

2. Prior Art

In U.S. Pat. Nos. 3,840,597, 3,856,859 and 3,906,024 and Japanese Patent Kokai No. 10,584, there are disclosed sulfonamide compounds having substituted phenyl groups via an oxygen atom or a sulfur atom and showing anti-inflammatory effect [e.g., N-(4-nitro-2-phenoxy-phenyl)methanesulfonamide].

However, there is a problem that drugs showing anti-inflammatory effect have gastrointestinal injuries as clinical side effects.

SUMMARY OF THE INVENTION

As a result of the earnest research for the purpose of the above, the present inventors have found the compounds showing anti-inflammatory, antipyretic and analgesic effects and further showing the decrease of side effects such as gastrointestinal injuries, and accomplished the present invention.

According to the present invention, there is provided sulfonanilide compounds represented by the formula

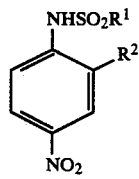

I wherein $R^1$ is a lower alkyl group or a trifluoromethyl group, $R^2$ is a cycloalkylidenemethyl group, a group of the formula —A—$R^3$ (wherein A is an oxygen atom, a sulfur atom, a sulfinyl group or a sulfonyl group and $R^3$ is a cycloalkyl group having 5–8 carbon atoms; a cycloalkyl group having 5–8 carbon atoms substituted by one or two of a lower alkyl group, an oxo group, a hydroxyl group or a methanesulfonyloxy group; a tetrahydropyranyl group; a tetrahydrothiopyranyl group; or a 1-methylpiperidyl group) or a group of the formula —B—$R^4$ (wherein B is a carbonyl group, a hydroxymethylene group or a methylene group, $R^4$ is a cycloalkyl group having 5–8 carbon atoms) and the pharmaceutically acceptable salts thereof.

BRIEF DESCRIPTION OF THE DRAWING

FIG. 1 shows the body weight change in Experiment 2.

DETAILED DESCRIPTION OF THE INVENTION

In the present invention, the cycloalkylidenemethyl group refers to a cyclopentylidenemethyl group, a cyclohexylidenemethyl group and the like. The lower alkyl group refers to a lower alkyl group having 1 to 4 carbon atoms such as, for example, a methyl group, an ethyl group, a propyl group, an isopropyl group, a butyl group, a tert-butyl group and the like, and the cycloalkyl group having 5–8 carbon atoms refers to a cyclopentyl group, a cyclohexyl group, a cycloheptyl group and a cyclooctyl group.

The pharmaceutically acceptable salt refers to inorganic salts such as a lithium salt, a sodium salt, a potassium salt, a calcium salt and the like, and salts with organic amines such as triethylamine, ethanolamine and the like.

Among the preferred compounds of the present invention are compounds of Formula I wherein $R^1$ is a methyl group or a trifluoromethyl group, $R^2$ is a cyclopentyloxy group, a cyclohexyloxy group, a cyclopentylthio group and a tetrahydro-4H-thiopyranyloxy group.

The compounds of Formula I can be prepared, for example, from known compounds according to the following methods.

(1) A compound of Formula I wherein $R^2$ is —A—$R^3$ (wherein A is an oxygen atom or a sulfur atom) can be prepared from a 2-halonitrobenzene as a starting material.

Namely, a 2-halonitrobenzene is reacted with a compound of the formula $R^3$—YH (wherein $R^3$ is as defined above, and Y is an oxygen atom or a sulfur atom) in the presence of a base and/or copper to give a compound of the formula

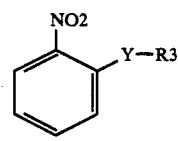

II (wherein Y and $R^3$ are as defined above).

Examples of the base used in the reaction are alkali hydroxides such as sodium hydroxide, potassium hydroxide and the like, alkali hydrides such as sodium hydride, potassium hydride and the like, alkali carbonates such as sodium carbonate, potassium carbonate and the like, and alcoholates such as sodium ethoxide, potassium tert-butoxide and the like.

Next, the compound of Formula II is reduced to give an amino form. The reduction may be an ordinary reduction by which a nitro group is reduced to an amino group, for example, catalytic reduction using palladium or platinum, or reduction using iron, tin, sodium sulfide-ammonium chloride, sodium borohydride or lithium aluminum hydride.

Subsequently, the amino form obtained above is reacted with a compound of the formula $R^1SO_2X$ or $(R^1SO_2)_2O$ (wherein $R^1$ is as defined above, and X is a fluorine atom, a chlorine atom, a bromine atom or an iodine atom) to give a sulfonanilide form, which is then nitrated to give a compound of the present invention represented by the formula

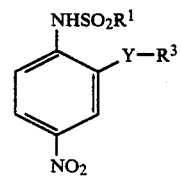

III wherein $R^1$, $R^3$ and Y are as defined above.

(2) A compound of Formula I wherein $R^2$ is —O—$R^3$ can be also obtained from 2-hydroxy-4-nitroaniline as a starting material. Namely, 2-hydroxy-4- nitroaniline is reacted with a compound of the formula R³—X (wherein R³ and X are as defined above.) in the presence of a base and followed by reacting with a compound of the formula R¹SO₂X or (R¹SO₂)₂O (wherein R¹ and X are as defined above.) to give a compound of Formula I.

(3) A compound of Formula I wherein R² is —A—R³ (wherein A is as defined above, and R³ is a cycloalkyl group substituted by a hydroxyl group) can be prepared according to the following method. That is, this compound can be prepared by reducing the compound of Formula I wherein R³ is an oxocycloalkyl group, obtained in the method of item (1). The reduction used in this reaction may be an ordinary reduction by which a ketone is converted to an alcohol, for example, a reduction using sodium borohydride, lithium aluminum hydride, diborane, lithium, sodium and the like.

(4) A compound of Formula I wherein R² is —A—R³ (wherein A is as defined above, and R³ is an oxocycloalkyl group) can be also prepared according to the following method.

More particularly, this compound can be prepared by oxidizing a compound represented by the formula

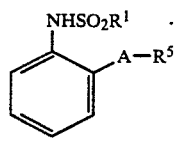
IV wherein R¹ and A are as defined above, R⁵ is a cycloalkyl group substituted by a hydroxyl group, obtained in the item (1), and then subjecting to a nitration similar to that of the item (1). The oxidation used in this reaction may be an ordinary oxidation by which an alcohol is converted to a ketone, for example, methods using chromium trioxide (Jones reagent, Collins reagent and the like), potassium permanganate, manganese dioxide, dimethyl sulfoxide and the like.

(5) A compound of Formula I wherein R² is —A—R³ (wherein A is a sulfinyl group or a sulfonyl group) can be prepared by oxidizing the compound of Formula I wherein R² is —S—R³ obtained in the above item (1) in accordance with an ordinary oxidation, for example, methods using hydrogen peroxide, peracetic acid, m-chloroperbenzoic acid, potassium permanganate, sodium periodate and the like.

(6) A compound of Formula I wherein B is a carbonyl group can be prepared from 2-aminobenzonitrile as a starting material. More specially, 2-aminobenzonitrile is reacted with an organometallic compound containing the group R⁴, and hydrolyzed to give a 2-cycloalkylcarbonylaniline compound. Examples of the organometallic compound containing the group R⁴ in this reaction are Grignard reagents, organolithium compound or organocopper compounds such as cyclopentyl magnesium bromide, cyclohexylmagnesium chloride, cyclohexylmagnesium bromide, cyclopentyllithium, cyclohexyllithium, lithium dicyclohexyl cuprate and the like.

Next, the 2-cycloalkylcarbonylaniline compound is subjected, in turn, to sulfonation and nitration similar to those of the item (1) to give a compound of Formula I wherein B is a carbonyl group.

(7) A compound of Formula I wherein B is a hydroxymethylene group can be prepared by reduction of the compound of Formula I wherein B is a carbonyl group obtained in the item (6). The reduction used may be a reaction similar to that of the item (3).

(8) The compound of Formula I wherein R² is a cycloalkylidenemethyl group can be prepared by dehydration of the compound of Formula I wherein B is a hydroxymethylene group obtained in the item (7). The dehydration in this reaction may be an ordinary method by which an alcohol is converted to an olefin, for example, a method using potassium hydrogen sulfate, sulfuric acid, phosphoric acid, acetic anhydride, phthalic anhydride, thionyl chloride-pyridine, phosphorus oxychloride-pyridine and the like.

(9) A compound of Formula I wherein B is a methylene group can be prepared by a following process. Namely, the compound of Formula I wherein R² is a cycloalkylidenemethyl group obtained in the item (8) is subjected to catalytic reduction to give a compound of the formula

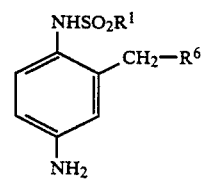
V wherein R¹ is as defined above, and R⁶ is a cycloalkyl group.

Subsequently, the compound of Formula V can be oxidized according to an ordinary method by which an amino group is converted to a nitro group, and there is obtained a compound of Formula I wherein B is a methylene group. Examples of the oxidation used are those using potassium permanganate, hydrogen peroxide, trifluoroperacetic acid, sodium nitrite-copper (I) oxide and the like.

(10) The pharmaceutically acceptable salts of the compound of Formula I can be prepared by treating the compound of Formula I with a base in water or an organic solvent. Examples of the base used in this reaction are hydroxides such as lithium hydroxide, sodium hydroxide, potassium hydroxide and the like, alcoholates such as sodium ethoxide, potassium tert-butoxide and the like, organic amines such as triethylamine and ethanolamine.

The compounds of the present invention show anti-inflammatory, antipyretic and analgesic activities and then show lower side effects in the toxicity study concerning gastrointestinal injuries and anemia comparing with the prior art compounds. Therefore, these compounds are useful as anti-inflammatory agent, antipyretic agent and analgesic agent. For these purposes, these compounds can be administered orally or parenterally in conventional dosage forms such as tables, powder, granules, capsules, solutions, emulsions, suspensions and injectionable preparations, all of which can be prepared by ordinary preparation processes.

When the compound of Formula I is used as anti-inflammatory agent, antipyretic agent or analgesic agent to human, the dose depends on the age, body weight and symptom of patient, the route of administration, time of administration and the like, but usually it may be from 10 to 2000 mg per day.

The compounds of the present invention is illustrated by the following experiments.

Experiment 1 [Edema inhibition test using carrageenin]

Six male Wistar strain rats were administered orally the compounds of the present invention for each group, and ibuprofen was used as a comparative drug. The $ED_{30}$ values of the edema inhibition were obtained according to the method of Winter et al. in Journal of Pharmacology and Experimental therapeutics, vol. 141, page 369 (1963) using carrageenin.

The results are shown in Table 1

TABLE 1

| compound | $ED_{30}$ value (mg/kg) |
|---|---|
| a | 1.2 |
| b | 5.0 |
| c | 12.0 |
| d | 8.6 |
| ibuprofen | 19.3 |

(note)
a: N—(2-cyclohexyloxy-4-nitrophenyl)methanesulfonamide.
b: N—(2-cyclohexyloxy-4-nitrophenyl)trifluoromethane-sulfonamide.
c: N—[2-(cyclopentylthio)-4-nitrophenyl]methane-sulfonamide.
d: N—[4-nitro-2-(tetrahydro-4H—thiopyran-4-yloxy)-phenyl]trifluoromethanesulfonamide Experiment 2 [14-day oral toxicity study in rats]

Seven male Wistar strain rats, weighing 151.1 to 173.9 g were used as test animals for each group.

N-(2-cyclohexyloxy-4-nitrophenyl)methanesulfonamide (hereinafter referred to as "Compound 1") suspended in a 5% aqueous gum arabic solution was administered orally in a dose level of each 75 mg/kg and 150 mg/kg once a day for 14 consecutive days at a constant dose volume of 0.5 ml per 100 g of body weight.

75 mg/kg and 150 mg/kg of N-(4-nitro-2-phenoxyphenyl)methanesulfonamide (hereinafter referred to as "Comparative drug 1") and 150 mg/kg of ibuprofen (hereinafter referred to as "Comparative drug 2") were administered orally similary as comparative drugs for comparison of the toxicity.

A 5% aqueous gum arabic solution only was administered orally similarly as a control group.

<Results>

(1) General Conditions, Fatality and Changes of Body Weight

Change of body weight and fatality are shown in FIG. 1 and Table 2, respectively.

Change of general conditions, change of body weight and fatality during the administration period were not observed in each of the groups treated with Compound 1. Anemic symptoms (paling of ear wings, eyeballs and the ends of limbs) and the decrease of the body weight or the inhibition of the body weight gain were observed from the beginning of the administration period in each of the groups treated with Comparative drug 1 and the group treated with Comparative drug 2. There were observed fatalities of one of 7 animals of the group treated with Comparative drug 1 (75 mg/kg) and fatalities of 6 of 7 animals of the group treated with Comparative drug 1 (150 mg/kg). Of these fatalities, the hemorrhage on the gastric mucosa and multiple ulcer on the lower area of the small intestine were found by the autopsic observation.

TABLE 2

| | | Fatality (day) | | | | | | | | | | | | | | Fatality |
|---|---|---|---|---|---|---|---|---|---|---|---|---|---|---|---|---|
| (mg/kg) | | 1 | 2 | 3 | 4 | 5 | 6 | 7 | 8 | 9 | 10 | 11 | 12 | 13 | 14 | |
| Control | | | | | | | | | | | | | | | | |
| Compound 1 | 75 | | | | | | | | | | | | | | | 0 |
| | 150 | | | | | | | | | | | | | | | 0 |
| Comparative drug 1 | 75 | | | | | | | | 1 | 1 | | | | | | |
| | 150 | 1 | | | 1 | 2 | | | | 1 | 1 | 6 | | | | |
| Comparative drug 1 | 150 | | | | | | | | | | | | | | | 0 |

(2) Hematological and Biochemical Examinations

The decreases of number of the red blood cell, the hemoglobin volume and the hematocrit value as main changes were found in each of the groups treated with Comparative drug 1 and the group treated with Comparative drug 2 (Table 3).

On the other hand, no above-mentioned changes were found in each of the groups treated with Compound 1.

TABLE 3

| | Hematological Examination | | | | | |
|---|---|---|---|---|---|---|
| | Control | Compound 1 | | Comparative drug 1 | | Comparative drug 2 |
| (mg/kg) | | 75 | 150 | 75 | 150 | 150 |
| Number of red blood cell ($10^6 \times$ mm$^3$) | (7) 9.33 ±0.53 | (7) 9.33 ±0.45 | (7) 9.52 ±0.96 | (6) 7.23* ±0.81 | (1) 5.72 | (7) 6.66** ±1.02 |
| hemoglobin volume (g/dl) | 17.3 ±1.0 | 17.1 ±0.7 | 17.1 ±1.2 | 13.2** ±2.2 | 9.6 | 11.2** ±2.2 |
| hematocrit value (%) | 47.9 ±2.8 | 48.0 ±2.0 | 48.7 ±4.8 | 37.6 ±6.2 | 27.8 | 32.2** ±6.1 |

Mean ±SD, ( ): number of animals
*p < 0.05, **p < 0.01

(3) Pathological Examination

By main autopsic observations of the survival, multiple ulcer on the lower area of the small intestine and swelling on the mesenteric lymph nodes were found in each of the groups treated with Comparative drug 1 and the group treated with Comparative drug 2.

Changes of absolute and relative weights of organs were shown in Table 4. The increases of weights of the spleen and the mesenteric lymph nodes were observed in each of the groups treated with Comparative drug 1 and the group treated with Comparative drug 2.

No above-mentioned changes were found in the group treated with Compound 1.

TABLE 4

| | Organ weight | | | | | |
|---|---|---|---|---|---|---|
| | Control | Compound 1 | | Comparative drug 1 | | Comparative drug 2 |
| (mg/kg) | | 75 | 150 | 75 | 150 | 150 |
| spleen Ab (mg) | (7) 477 ±23 | (7) 479 ±29 | (7) 516 ±63 | (6) 644* ±93 | (1) 587 | (7) 732** ±139 |
| Rel (mg %) | 215 ±8 | 220 ±8 | 233 ±22 | 363** ±111 | 423 | 382** ±75 |
| mesenteric lymph nodes Ab (mg) | 78 ±17 | 85 ±14 | 98 ±17 | 246** ±92 | 392 | 213** ±32 |
| Rel (mg %) | 35 | 35 | 44 | 142** | 287 | 111** |

TABLE 4-continued

| (mg/kg) | Control | Compound 1 | | Comparative drug 1 | | Comparative drug 2 |
|---|---|---|---|---|---|---|
| | | 75 | 150 | 75 | 150 | 150 |
| | ±8 | ±6 | ±7 | ±92 | | ±14 |

Mean ± SD, ( ): number of animals
*p < 0.05, **p < 0.01
Ab: absolute weight, Rel: relative weight The present invention is illustrated by the following examples in more detail.

EXAMPLE 1

(1) To 40 ml of a dioxane suspension containing 0.92 g of 60% sodium hydride was added 2.5 ml of cyclohexanol at room temperature over a 15-minute period, and the mixture was stirred at the same temperature for 1 hour and then at 50° C. for 3.5 hours. The temperature of the reaction solution was returned to room temperature, 10 ml of a dioxane containing 3.2 g of 2-fluoronitrobenzene was added dropwise, and the mixture was stirred at room temperature overnight. The dioxane was evaporated, the residue was extracted with chloroform, and the chloroform layer was washed, in turn, with water and a saturated aqueous sodium chloride solution and then dried over anhydrous sodium sulfate. The solvent was evaporated to give an oil, which was then distilled under reduced pressure to give 3.8 g of 2-cyclohexyloxynitrobenzene.

b.p. 130°–134° C./0.5–0.7 mmHg (2) Fifty ml of a methanol solution containing 3.7 g of 2-cyclohexyloxynitrobenzene and 0.2 g of 5% palladium on carbon was stirred at room temperature under a hydrogen atmosphere for catalytic reduction. The catalyst was removed by filtration, and the filtrate was evaporated off to give 2.9 g of 2-cyclohexyloxyaniline as pale brown crystals.

m.p. 55°–56° C.

(3) To 20 ml of a pyridine solution containing 2.7 g of 2-cyclohexyloxyaniline was added dropwise 1.8 g of methanesulfonyl chloride under ice cooling with stirring. After completion of the addition, the mixture was stirred at room temperature for 2 hours. The reaction solution was poured into ice water and made acidic with dilute hydrochloric acid. The crystals which formed were collected by filtration, washed with water and dried to give 3.8 g of the crude crystals, which were then recrystallized from ethanol-n hexane to give 3.4 g of N-(2-cyclohexyloxyphenyl)methanesulfonamide.

m.p. 113°–115° C.

(4) To 20 ml of an acetic acid solution containing 3.4 g of N-(2-cyclohexyloxyphenyl)methanesulfonamide was added dropwise 1.5 g of 61% nitric acid on heating at 110° C. over a 30-minute period, and then the mixture was stirred for 1 hour. The reaction solution was poured into ice water and neutralized with a dilute aqueous sodium hydroxide solution. The crystals which formed were collected by filtration, washed with water and dried to give 4.5 g of the crude crystals, which were then recrystallized from ethanol-n-hexane to give 3.3 g of N-(2-cyclohexyloxy-4-nitrophenyl)methanesulfonamide.

m.p. 136°–137° C.

Following the procedure similar to that of Example 1, there were the following compounds.

N-(2-cyclopentyloxy-4-nitrophenyl)methanesulfonamide m.p. 155.5°–157.5° C.

N-(2-neomenthyloxy-4-nitrophenyl)methanesulfonamide m.p. 127.5°–129° C.

N-(2-l-menthyloxy-4-nitrophenyl)methanesulfonamide m.p. 109°–111° C.

N-[2-(trans-2-methylcyclohexyloxy)-4-nitrophenyl]methanesulfonamide m.p. 87°–88° C.

N-[2-(cis-2-methylcyclohexyloxy)-4-nitrophenyl]methanesulfonamide m.p. 93°–94° C.

N-[2-(3-methylcyclohexyloxy)-4-nitrophenyl]methanesulfonamide m.p. 95°–96° C.

N-[2-(4-methylcyclohexyloxy)-4-nitrophenyl]methanesulfonamide m.p. 136°–137° C.

N-[2-(1-methylpiperidin-4-yloxy)-4-nitrophenyl]methanesulfonamide m.p. 165°–166° C.

N-[4-nitro-2-(tetrahydro-4H-pyran-4-yloxy)phenyl]methanesulfonamide m.p. 183°–184° C.

N-[2-(2-hydroxycyclohexyloxy)-4-nitrophenyl]methanesulfonamide m.p. 142°–145° C.

N-[2-(2-methanesulfonyloxycyclohexyloxy)-4-nitrophenyl]methanesulfonamide m.p. 168°–172° C.

N-(2-cycloheptyloxy-4-nitrophenyl)methanesulfonamide m.p. 113.5°–114.5° C.

EXAMPLE 2

(1) A mixture of 7.4 g of cyclohexanethiol, 4.2 g of potassium hydroxide and 70 ml of methanol was stirred at room temperature until the potassium hydroxide was dissolved. After evaporation of the solvent under reduced pressure, 100 ml of dioxane as added, and then 20 ml of a dioxane solution containing 6.0 g of 2-fluoronitrobenzene was added dropwise under ice cooling with stirring. After completion of the addition, the mixture was stirred at room temperature for 45 minutes, and the reaction solution was poured into a dilute aqueous sodium hydroxide solution and extracted with ethyl ether. The ethyl ether layer was washed, in turn, with a dilute aqueous sodium hydroxide solution, water and a saturated aqueous sodium chloride solution, and dried over anhydrous sodium sulfate. The ethyl ether layer was evaporated to give 10.9 g of a yellow oil, which was then purified by silica gel column chromatography (eluent; n-hexane:dichloromethane=14:1–n-hexane:ethyl acetate=19:1) to give 9.2 g of 2-(cyclohexylthio)nitrobenzene as a yellow oil.

b.p. 144°–146° C./0.8 mmHg.

(2) A mixture of 8.5 g of 2-(cyclohexylthio)nitrobenzene, 9.6 g of iron powder, 0.61 g of ammonium chloride and 22 ml of water was stirred on heating at 90° C. for 3 hours. The temperature of the reaction solution was returned to room temperature, the reaction solution was filtered by Selite and extracted with dichloromethane. The dichloromethane layer was washed, in turn, with water and a saturated aqueous sodium chloride solution and dried over anhydrous sodium sulfate. The solvent was evaporated to give 7.3 g of 2-(cyclohexylthio)aniline as a yellow oil.

b.p. 126°–128° C./1.6 mmHg.

(3) To 35 ml of a pyridine solution containing 3.5 of 2-(cyclohexylthio)aniline was added dropwise 3.9 g of methanesulfonyl chloride under ice cooling, and the mixture was stirred for 1.5 hours. The reaction solution was poured into ice water, made acidic with dilute hydrochloric acid and extracted with dichloromethane. The dichloromethane layer was washed, in turn, with water and a saturated aqueous sodium chloride solution and dried over anhydrous sodium sulfate. The solvent was evaporated to give 5.8 g of a yellowish brown oil, which was then purified by silica gel column chromatography (eluent:n-hexane:ethyl acetate=9:1) and then by recrystallization from carbon tetrachloride-n-hexane to give 4.0 g of N-[2-(cyclohexylthio)phenyl]methanesulfonamide.

m.p. 50°–51° C.

(4) To 10 ml of an acetic acid solution containing 1.0 g of N-[2-(cyclohexylthio)phenyl]methanesulfonamide was added dropwise 0.41 g of 61% nitric acid under heating at 65° C., and the mixture was stirred under heating for 1 hour. The temperature of the reaction solution was returned to room temperature, and the reaction solution was poured into ice water, neutralized with a dilute aqueous sodium hydroxide solution and extracted with dichloromethane. The dichloromethae layer was washed, in turn, with water and a saturated aqueous sodium chloride solution and dried over anhydrous sodium sulfate. The solvent was evaporated to give 1.6 g of reddish brown crude crystals, which were purified by silica gel column chromatography (eluent:n-hexanedichloromethane=1:1) to give 0.6 g of pale yellow crystals, which were then recrystallized from n-hexaneethyl acetate to give 0.52 g of N-[2-(cyclohexylthio)-4-nitrophenyl]methanesulfonamide as colorless crystals.

m.p. 139.5°–140.5° C.

Following the procedure of that of Example 2, there was obtained the following compound.

N-(2-cyclopentylthio)-4-nitrophenyl)methanesulfonamide m.p. 134.5°–135.5° C.

EXAMPLE 3

To 60 ml of a chloroform solution containing 2.0 g of N-[2-(cyclohexylthio)-4-nitrophenyl]methanesulfonamide obtained in Example 2 was added dropwise 20 ml of a chloroform solution containing 1.4 g of m-chloroperbenzoic acid at −20° to −10° C. over a 3-minute period, and then the mixture was stirred for 6 minutes. The reaction solution was poured into ice water, neutralized with a dilute aqueous sodium hydroxide solution and extracted with chloroform. The chloroform layer was washed, in turn, with water and a saturated aqueous sodium chloride solution, and dried over anhydrous sodium sulfate. The solvent was evaporated to give 2.1 g of the crude crystals, which were then purified by silica gel column chromatography (eluent: chloroform-methanol=10:1) and then by recrystallization from n-hexane-ethyl acetate to give 1.7 g of N-(2-cyclohexylsufinyl-4-nitrophenyl)methanesulfonamide as pale yellow crystals.

m.p. 197°–199° C.

EXAMPLE 4

To 20 ml of a chloroform solution of 1.2 g of N-(2-cyclohexylsulfinyl-4-nitrophenyl)methanesulfonamide obtained in Example 3 was added dropwise 60 ml of a chloroform solution containing 3.9 g of m-chloroperbenzoic acid under ice cooling with stirring. The mixture was stirred for 3 hours. The reaction solution was poured into ice water, neutralized with a dilute aqueous sodium hydroxide solution and extracted with chloroform. The chloroform layer was washed, in turn, with water and a saturated aqueous sodium chloride solution and dried over anhydrous sodium sulfate. The solvent was evaporated to give the crude crystals, which were washed with ethyl ether and then recrystallized from ethyl acetate-n-hexane to give 1.1 g of N-(2-cyclohexylsulfonyl-4-nitrophenyl)methanesulfonamide as pale yellow crystals.

m.p. 185.5°–186.5° C.

EXAMPLE 5

(1) Following reactions similar to those of Example 1 (1), 1 (2) and 1 (3), there was obtained N-[2-(1,4-dioxaspiro[4,5]decan-8-yloxy)phenyl]methanesulfonamide from 1,4-dioxaspiro[4,5]decan-8-ol.

m.p. 128°–129° C.

(2) Following a reaction similar to that of Example 1 (4) using 1.0 g of N-[2-(1,4-dioxaspiro[4,5]-decan-8-yloxy)phenyl]methanesulfonamide, there was obtained 0.47 g of N-[4-nitro-2-(4-oxocyclohexyloxy)phenyl]methanesulfonamide.

m.p. 152.5°–153.5° C.

EXAMPLE 6

To 8 ml of a mixture of methanol and tetrahydrofuran (1:2) containing 0.23 g of N-[4-nitro-2-(4-oxocyclohexyloxy)phenyl]methanesulfonamide obtained in Example 5 (2) was added 0.01 g of sodium borohydride under ice cooling, and the mixture was stirred for 20 minutes. To the reaction solution was a dilute hydrochloric acid, and the mixture was extracted with ethyl acetate. The ethyl acetate layer was washed, in turn, with water and a saturated aqueous sodium chloride solution and dried over anhydrous magnesium sulfate. The solvent was evaporated, and the resulting residue was purified by silica gel column chromatography (eluent; n-hexane:dichloromethane:ethyl acetate=1:1:1) and then by recrystallization from dichloromethane-n-hexane to give 0.17 g of N-[2-(4-hydroxycyclohexyloxy)-4-nitrophenyl]methanesulfonamide.

m.p. 141°–145° C.

EXAMPLE 7

(1) Following procedures similar to those of Example 1 (1), 1, (2) and 1 (3), there was obtained N-[2-(2-hydroxycyclohexyloxy) phenyl]methanesulfonamide for 1,2-cyclohexanediol.

m.p. 151°–154° C.

(2) To 10 ml of an acetone solution containing 0.50 g of N-[2-(2-hydroxycyclohexyloxy)phenyl]methanesulfonamide was added 0.5 g of 8N Jones reagent (chromic acid-sulfuric acid) under ice cooling with stirring, and the mixture was stirred for 1 hour. Then, to the reaction solution was added 1 ml of isopropyl alcohol and water, and the mixture was extracted with dichloromethane. The dichloromethane layer was washed, in turn, with water and a saturated aqueous sodium chloride solution, and dried over anhydrous magnesium sulfate. The solvent was evaporated, and the resulting residue was purified by silica gel column chromatography (eluent; n-hexane:dichloromethane=1:1) and then recrystallized from ethanol-n-hexane to give 0.21 g of N-[2-(2-oxocyclohexyloxy)phenyl]methanesulfonamide.

m.p. 104°–106° C.

(3) Following a reaction similar to that of Example 1 (4), there was obtained 0.15 g of N-[4-nitro-2-(2-oxocyclohexyloxy)phenyl]methanesulfonamide from 0.20 g of N-[2-(2-oxocyclohexyloxy)phenyl]methanesulfonamide.

m.p. 192°–194° C.

EXAMPLE 8

(1) To 50 ml of a dioxane suspension containing 0.96 g of 60% sodium hydride was added 3.6 g of 4-hydroxytetrahydrothiopyran at room temperature, and the mixture was stirred on heating at 90° C. with stirring for 6 hours. The temperature of the mixture was returned to room temperature, then 10 ml of a dioxane solution of 4.5 g of 2-fluoronitrobenzene was added dropwise, and the mixture was stirred overnight. The reaction solution was poured into ice water and extracted with ethyl ether, and the ethyl ether layer was washed, in turn, with water and a saturated aqueous sodium chloride solution, and dried over anhydrous sodium sulfate. The solvent was evaporated, and 1.1 g of the resulting oil was purified by silica gel column chromatography (eluent; n-hexane:ethyl acetate=10:1 ) to give 6.1 g of 2-(tetrahydro-4H-thiopyran-4-yloxy)nitrobenzene as a pale yellow oil.

$^1$H-NMR (CDCl$_3$) δ: 2.04–2.27 (4H, m), 2.44–2.60 (2H, m), 2.92–3.12 (2H, m), 4.55–4.68 (1H, m), 6.97–7.11 (2H, m), 7.46–7.58 (1H, m), 7.82 (1H, dd, J=8 Hz, 1 Hz)

(2) Following a reaction similar to that of Example 1 (2) using 5.0 g of 2-(tetrahydro-4H-thiopyran-4-yloxy)-nitrobenzene, iron powder and ammonium chloride, there was obtained 4.3 g of 2-(tetrahydro-4H-thiopyran-4-yloxy)aniline.

$^1$H-NMR (CDCl$_3$) δ: 1.94–2.15 (2H, m), 2.16–2.35 (2H, m), 2.52–2.69 (2H, m), 2.83–3.00 (2H, m), 3.81 (2H, bs), 4.27–4.42 (1H, m), 6.63–6.89 (4H, m).

(3) Following a reaction similar to that of Example 1 (3) using 2.0 g of 2-(tetrahydro-4H-thiopyran-4-yloxy)aniline, there was obtained 2.5 g of N-[2-(tetrahydro-4H-thiopyran-4-yloxy)phenyl]methanesulfonamide.

$^1$H-NMR (CDCl$_3$) δ: 1.87–2.08 (2H, m), 2.25–2.42 (2H, m), 2.61–2.92 (4H, m), 2.98 (3H, s), 4.31–4.45 (1H, m), 6.81 (1H, bs), 6.86–6.97 (1H, m), 7.00 (1H, dd, J=8 Hz, 1 Hz), 7.07–7.18 (1H, m), 7.56 (1H, dd, J=8 Hz, 1 Hz).

(4) Following a reaction similar to that of Example 1 (4) using 1.5 g of 2-(tetrahydro-4H-thiopyran-4-yloxy)-phenyl]methanesulfonamide, there was obtained 0.88 g of N-[4-nitro-2-(tetrahydro-4H-thiopyran-4-yloxy)-phenyl]methanesulfonamide.

m.p. 200°–200.5° C.

EXAMPLE 9

(1) In 10 ml of pyridine was dissolved 2.0 g of 2-(cyclohexylthio)aniline obtained in Example 2 (2), 1.2 g of ethanesulfonyl chloride was added dropwise under ice cooling, and then the mixture was stirred at room temperature overnight. The reaction solution was poured into ice water, made acidic with dilute hydrochloric acid, and extracted with ethyl acetate. The ethyl acetate layer was washed, in turn, with water and a saturated aqueous sodium chloride solution, and dried over anhydrous magnesium sulfate. The solvent was evaporated, and the resulting residue was purified by silica gel column chromatography (eluent:n-hexaneethyl acetate=10:1) to give 2.7 g of N-[2-(cyclohexylthio)phenyl]ethanesulfonamide as an oil.

$^1$H-NMR (CDCl$_3$) δ: 1.06–1.49 (5H, m), 1.35 (3H, t, J=7 Hz), 1.51–2.01 (5H, m), 2.83–3.04 (1H, m), 3.15 (2H, q, J=7 Hz), 7.08 (1H, dt, J=8 Hz, 2 Hz), 7.35 (1H, dt, J=8 Hz, 2 Hz), 7.55 (1H, dt, J=8 Hz, 2 Hz), 7.66 (1H, dt, J=8 Hz, 2 Hz), 7.84 (1H, s).

(2) In 20 ml of acetic acid was dissolved 1.5 g of N-[2-(cyclohexylthio)phenyl]ethanesulfonamide, 0.33 g of 61% nitric acid was added dropwise on heating at 80°–85° C., and then the mixture was stirred on heating for 1 hour. The reaction solution was poured into ice water, neutralized with a saturated sodium hydrogen carbonate solution and extracted with dichloromethane. The dichloromethane layer was washed, in turn, with a saturated aqueous sodium hydrogen carbonate solution, water and a saturated aqueous sodium chloride solution, and dried over anhydrous magnesium sulfate. The solvent was evaporated, and the resulting crude crystals were purified by silica gel column chromatography (eluent: n-hexane:dichloromethane:ethyl acetate=20:10:1) and recrystallized from carbon tetrachloride-n-hexane to give 1.1 g of N-(2-cyclohexylthio-4-nitrophenyl)ethanesulfonamide.

m.p. 119°–120.5° C.

EXAMPLE 10

Following a reaction similar to that of Example 9, there was obtained N-(2-cyclohexyloxy-4-nitrophenyl)ethanesulfonamide.

m.p. 94°–95° C.

EXAMPLE 11

(1) A mixture of 6.1 g of 2-cyclohexyloxyaniline obtained in Example 1 (2), 5.4 ml of triethylamine and 60 ml of dichloromethane was cooled to −5°–0° C., and 10 ml of a dichloromethane solution containing 10 g of trifluoromethanesulfonic anhydride was added dropwise with stirring over a 20-minute period. The mixture was stirred for 3 hours while gradually returning the temperature of the mixture to room temperature, and then the reaction solution was poured into ice water and extracted with chloroform. The chloroform layer was washed, in turn, with water and a saturated aqueous sodium chloride solution, and dried over anhydrous magnesium sulfate. The solvent was evaporated, and 9.8 g of the resulting crude crystals were recrystallized from ethyl acetate-n-hexane to give 8.6 g of N-(2-cyclohexyloxyphenyl)trifluoromethanesulfonamide.

m.p. 83°–85° C.

(2) Following a reaction similar to that of Example 1 (4) using 7.5 g of N-(2-cyclohexyloxyphenyl)trifluoromethanesulfonamide, there was obtained 5.8 g of N-(2-cyclohexyloxy-4-nitrophenyl)trifluoromethanesulfonamide.

m.p. 93.5°–95° C.

Following a reaction similar to that of Example 11, there were obtained the following compounds.

N-(2-cyclopentyloxy-4-nitrophenyl)trifluoromethanesulfonamide m.p. 93.5°–95° C.

N-(2-l-menthyloxy-4-nitrophenyl)trifluoromethanesulfonamide m.p. 110.5°–111.5° C.

N-(4-nitro-2-(tetrahydro-4H-thiopyran-4-yloxy)-phenyl]trifluoromethanesulfonamide m.p. 114.5°–115.5° C.

N-(2-cyclohexylthio-4-nitrophenyl)trifluoromethanesulfonamide m.p 85°–86.5° C.

N-(2-cyclopentylthio-4-nitrophenyl)trifluoromethanesulfonamide $^1$H-NMR (CDCl$_3$) δ: 1.44–1.99 (6H, m), 1.95–2.16 (2H, m), 3.39–3.56 (1H, m), 7.82 (1H, d, J=9 Hz), 8.24 (1H, dd, J=9 Hz, 2 Hz), 8.44 (1H, bs), 8.47 (1H, d, J=2 Hz)

EXAMPLE 12

(1) 3.1 g of magnesium turnings, 10 ml of ethyl ether and several pieces of iodide were placed in a flask under a nitrogen gas, and the mixture was refluxed to fade out the color caused by iodide. 90 ml of an ethyl ether solution containing 20 g of cyclohexyl bromide was added dropwise over a 30-minute period under reflux with stirring. The temperature of the reaction solution was returned to room temperature, 40 ml of a tetrahydrofuran solution containing 4.8 g of 2-aminobenzonitrile was added dropwise over a 30-minute period, and the mixture was stirred for 30 minutes. 150 ml of an aqueous 1N hydrochloric acid solution was cautiously added, and the mixture was neutralized with a dilute aqueous sodium hydroxide solution and extracted with ethyl acetate. The ethyl acetate layer was washed, in turn, with water and a saturated aqueous sodium chloride solution and dried over anhydrous magnesium sulfate. The solvent was evaporated, and the resulting residue was purified by silica gel column chromatography (eluent; n-hexane:ethyl acetate=20:1) and recrystallized from ethyl acetate-n-hexane to give 6.2 g of 2-cyclohexylcarbonylaniline.

m.p. 74°-75° C.

(2) Following a reaction similar to that of Example 1 (3) using 2-cyclohexylcarbonylaniline, there was obtained N-(2-cyclohexylcarbonylphenyl)methanesulfonamide.

m.p. 119°-120° C.

(3) Following a reaction similar to that of Example 1 (4) using N-(2-cyclohexylcarbonylphenyl)methanesulfonamide, there was obtained N-(2-cyclo-hexylcarbonyl-4-nitrophenyl)methanesulfonamide.

m.p. 178°-179° C.

EXAMPLE 13

To 100 ml of a methanol solution containing 3.0 g of N-(2-cyclohexylcarbonylphenyl)methanesulfonamide obtained in Example 12 was added 0.35 g of sodium borohydride at room temperature with stirring, and the mixture was stirred for 1 hour. To the reaction solution was added 5 ml of acetone, and the mixture was neutralized with dilute hydrochloric acid. The solution was concentrated and extracted with ethyl acetate. The ethyl acetate layer was washed, in turn, with water and a saturated aqueous sodium chloride solution, and dried over anhydrous magnesium sulfate. The solvent was evaporated and the resulting crude crystals were recrystallized from ethyl acetate-n-hexane to give 2.8 g of N-(2-cyclohexylhydroxymethyl-4-nitrophenyl)methanesulfonamide.

m.p. 156°-157° C.

EXAMPLE 14

Fifty ml of a benzene solution containing 2.5 g of N-(2-cyclohexylhydroxymethyl-4-nitrophenyl)methanesulfonamide, obtained in Example 13, and 1.1 g of potassium hydrogen sulfate was refluxed for 1.5 hours. The temperature of the reaction solution was returned to room temperature, and then the solution was extracted with ethyl acetate. The ethyl acetate layer was washed, in turn, with water and a saturated aqueous sodium chloride solution and dried over anhydrous magnesium sulfate. The solvent was evaporated, and the resulting crude crystals were recrystallized from ethyl acetate-n-hexane to give 2.1 g of N-(2-cyclohexylidenemethyl-4-nitrophenyl)methanesulfonamide.

m.p. 174°-175° C.

EXAMPLE 15

(1) Fifty ml of an acetic acid solution containing 2.0 g of N-(2-cyclohexylidenemethyl-4-nitrophenyl)methanesulfonamide obtained in Example 14 and 0.1 g of platinum oxide was subjected to catalystic reduction under a hydrogen atmosphere at room temperature with stirring. The catalyst was removed by filtration, and the filtrate was concentrated, neutralized with a saturated aqueous sodium hydrogen carbonate solution and extracted with ethyl acetate. The ethyl acetate layer was washed, in turn, with water and a saturated aqueous sodium chloride solution and dried over anhydrous magnesium sulfate. Evaporation of the solvent gave 1.7 g of N-(4-amino-2-cyclohexylmethylphenyl)methanesulfonamide.

m.p. 160°-162° C.

(2) To 25 ml of a trifluoroacetic acid solution containing 1.5 g of N-(4-amino-2-cyclohexylmethylphenyl)methanesulfonamide was added dropwise 3 ml of a 30% aqueous hydrogen peroxide solution under reflux with stirring over a 30-minute period, and the mixture was stirred for a further 1 hour. The temperature of the reaction solution was returned to room temperature, and the solvent was evaporated. The residue was neutralized with a saturated aqueous sodium hydrogen carbonate solution and extracted with ethyl acetate, and then the ethyl acetate layer was washed, in turn, with water and a saturated aqueous sodium chloride solution and dried over anhydrous magnesium sulfate. The solvent was evaporated, and the resulting residue was purified by silica gel column chromatography (eluent: n-hexane:ethyl acetate=3:1) and then recrystallized from ethanol-n-hexane to give 0.25 g of N-(2-cyclohexyl-methyl-4-nitrophenyl)methanesulfonamide.

m.p. 142°-144° C.

EXAMPLE 16

To 20 ml of an ethanol solution containing 1.0 g of N-(2-cyclohexyloxy-4-nitrophenyl)methanesulfonamide obtained in Example 1 was added 3.2 ml of 1N sodium hydroxide at room temperature with stirring. The solvent was evaporated, and the resulting residue was recrystallized from ethanol-ethyl ether to give 1.0 g of sodium N-(2-cyclohexyloxy-4-nitrophenyl)methanesulfonamide.

m.p. 144°-158° C.

Following a reaction similar to that of Example 16, there was obtained the following compound.

Sodium N-(2-cyclohexyloxy-4-nitrophenyl)trifluoromethanesulfonamide m.p. 115°-118° C.

EXAMPLE 17

To 2 ml of an ethanol solution containing 0.2 g of sodium N-(2-cyclohexyloxy-4-nitrophenyl)methanesulfonamide obtained in Example 16 was added 0.6 ml of 1N calcium chloride at room temperature with stirring. The solvent was evaporated, and the resulting residue was recrystallized from water to give 0.17 g of calcium N-(2-cyclohexyloxy-4-nitrophenyl)methanesulfonamide.

m.p. 137°-142° C.

What is claimed is:

1. Sulfonanilide compounds represented by the formula

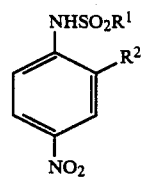

wherein $R^1$ is a lower alkyl group or a trifluoromethyl group, $R^2$ is a cycloalkylidenemethyl group, a group of the formula —A—$R^3$ (wherein A is an oxygen atom, a sulfur atom, a sulfinyl group or a sulfonyl group and $R^3$ is a cycloalkyl group having 5–8 carbon atoms; a cycloalkyl group having 5–8 carbon atoms substituted by one or two of a lower alkyl group, an oxo group, a hydroxyl group or a methanesulfonyloxy group; a tetrahydropyranyl group; a tetrahydrothiopyranyl group; or a 1-methylpiperidyl group) or a group of the formula —B—$R^4$ (wherein B is a carbonyl group, a hydroxymethylene group or a methylene group, $R^4$ is a cycloalkyl group having 5–8 carbon atoms) and the pharmaceutically acceptable salts thereof.

* * * * *